United States Patent [19]

Rantanen-Lee

[11] Patent Number: 5,035,399
[45] Date of Patent: Jul. 30, 1991

[54] PROTECTIVE TUBING CLAMP APPARATUS

[75] Inventor: Ann M. Rantanen-Lee, Sandy, Utah
[73] Assignee: C.R. Bard, Inc., Murray Hill, N.J.
[21] Appl. No.: 529,221
[22] Filed: May 25, 1990
[51] Int. Cl.⁵ .............................................. F16L 55/14
[52] U.S. Cl. .................................... 251/10; 604/250; 251/4
[58] Field of Search ........................ 251/4, 7, 8, 9, 10; 604/34, 250; 138/128

[56] References Cited

U.S. PATENT DOCUMENTS

| | | | |
|---|---|---|---|
| 3,316,935 | 5/1967 | Kaiser et al. | 135/595 |
| 3,942,228 | 3/1976 | Buckman et al. | 24/255 |
| 4,560,378 | 12/1985 | Weiland | 604/83 |
| 4,588,160 | 5/1986 | Flynn et al. | 251/10 |
| 4,589,626 | 5/1986 | Kurtz et al. | 251/10 |
| 4,623,102 | 11/1986 | Hough, Jr. | 248/68.1 |
| 4,643,389 | 2/1987 | Elson et al. | 251/10 |
| 4,673,161 | 6/1987 | Flynn et al. | 251/4 |
| 4,802,650 | 2/1989 | Stricker | 251/117 |
| 4,869,457 | 9/1989 | Ewerlöf | 251/6 |

Primary Examiner—Martin P. Schwadron
Assistant Examiner—Kevin L. Lee

[57] ABSTRACT

Disclosed is an apparatus for occluding resilient tubing which effectively and conveniently occludes tubing without damage to the tubing, even after repeated clamping. Included in embodiments of the invention are a clamping structure and a protective sleeve formed from a resilient material which is interposed between the tubing to be occluded and the clamp. Also included are structures to prevent the application of the clamp immediately adjacent to the ends of the tubing. Moreover, the clamp can be applied at any one of a plurality of positions along the tube so that no one location along the length of the tube is subject to excessive fatigue. The protective sleeve and the clamp are joined together such that the clamp cannot be applied to the tube without the protective sleeve interposed therebetween. The embodiments of the present invention prevent damage to tubing, such as fragile silicone rubber tubing used in medical applications, even when subjected to repeated clampings.

28 Claims, 2 Drawing Sheets

PROTECTIVE TUBING CLAMP APPARATUS

BACKGROUND

1. The Field of the Invention

This invention relates to tubing clamps. More particularly, the present invention relates to clamping structure which may be repeatedly opened and closed on a length of tubing without causing damage to the tubing.

2. The Prior Art

Flexible tubing fabricated from materials such as plastics and silicone rubber is widely used in many scientific, industrial, and in particular, medical applications. In the medical industry, flexible silicone tubing is fabricated into many different devices.

For example, silicone tubing is used to form one or more portions of in-dwelling catheter sets. Tubing is also used to provide interconnections between medical devices and between medical devices and a patient. Such tubing is often cylindrical but may have a substantially cylindrical shape or some other configuration.

Tubing, both that which is used in the medical industry and in other industries, must routinely be occluded to stop the flow of fluid (either a liquid or a gas under either positive or negative pressure) through the tube. For example, the flow of a medicament through a catheter is routinely stopped by manually applying a clamp to the catheter tubing.

In the medical field, the same properties (e.g., flexibility, small size, and the ability to form several lumens within a length of tubing) which makes silicone rubber particularly suitable for use as a catheter also makes silicone rubber catheters particularly susceptible to damage due to the pinching action of conventional tubing clamps when used alone. Repeated clamping of an unprotected flexible silicone rubber catheter often results in failure of the catheter. The failure of a silicone rubber catheter due to the repeated application of a clamp in a single location is at least very undesirable, and potentially life threatening. Moreover, if the wall thickness of the silicone rubber catheter is increased to provide strength against failure, the outer diameter of a catheter may be too large, and/or the inner too small, for some applications.

Several prior art attempts have been made in an effort to prevent undesirable failures of tubing due to the application of a clamp. One such currently known prior practice includes gluing a reinforcing sleeve at a single location on a length of tubing, such as a catheter, and to direct the user to apply a clamp only at that location. Nevertheless, such an arrangement still permits clamping to occur, both inadvertently and deliberately, at locations along the tubing other than at the location of the reinforcing sleeve.

Moreover, some portions of a length of tubing are more susceptible to damage from application of a clamp than others. For example, portions of tubing adjacent to connectors attached to the end of the tubing are particularly likely to fail if a clamp is applied thereto. Still further, even the inclusion of a reinforcing sleeve may not prevent damage due to repeated clamping at the same location. If clamping at a single location occurs repeatedly, the tubing may fail regardless of the interposition of a reinforcing sleeve and in some instances the reinforcing sleeve itself may fail.

The devices previously available in the art do little or nothing to address these long existing problems of tubing failure which persist even when a reinforced sleeve is attached to the tubing.

BRIEF SUMMARY AND OBJECTS OF THE INVENTION

In view of the foregoing described state of the art, it is a primary object of the present invention to provide an apparatus for clamping a tube which effectively and conveniently occludes a length of tubing without damaging the tubing even after repeated applications of the clamp.

It is another object of the present invention to provide an apparatus for clamping a tube which is particularly adapted for use with fragile tubing, medical tubing, thin wall tubing, and/or tubing which includes a plurality of internal lumens or channels.

It is still another object of the present invention to provide an apparatus for clamping a tube which allows the clamp to be positioned at any one of a plurality of positions along the length of tubing but yet prevent clamping at selected positions.

It is yet another object of the present invention to provide an apparatus for clamping a tube which both prevents damage to the tube from the action of the clamp and the misplacement and loss of the clamp itself.

These and other objects of the invention will become apparent by examining this disclosure and by practicing the invention.

The present invention provides an apparatus for occluding resilient tubing which effectively and conveniently occludes tubing without causing damage to the tubing, even after repeated clamping. The present invention includes structures which protect the tubing from damage by interposing a resilient material between the tubing and the clamping structure, assuring that the clamp is only applied at the protected portion of the tube, preventing the application of the clamp immediately adjacent to the ends of the tube, and allowing the clamp to be applied at any one of a plurality of positions along the length of tubing. 24 Included in the present invention is a means for compressing the wall of the resilient tubing. The means for compressing operates by squeezing the wall of the resilient tubing to occlude the one or more channels formed within the tubing. The means for compressing includes a compressing structure which is adapted to make occlusive contact with the resilient tubing.

The present invention also includes a means for protectively covering, which in some embodiments comprises a protective sleeve encircling a portion of the tubing. The means for protectively covering covers at least a portion of the outer wall of the tubing and preferably may comprise a resilient material.

The means for protectively covering, or the protective sleeve, can be positioned at any one of a plurality of positions along the length of tubing which is to be occluded. A means for connecting, or attaching, the means for compressing, or other clamping structure, to the means for protectively covering is also included in the embodiments of the present invention.

By connecting the clamping structure to the protective sleeve, the clamp cannot be separated and misplaced. Also, by connecting the clamping structure to the means for protectively covering, also referred to as a protective sleeve in some embodiments, the clamping action always occurs on a protected portion of the tubing. Moreover, the length of the protective sleeve may be selected so that the clamp cannot be applied within a predetermined distance of one or two stop structures formed at positions along the length of the tubing, such as connectors attached to the ends of the length of tubing.

DETAILED DESCRIPTION OF THE PREFERRED EMBODIMENTS

Reference will now be made to the drawings wherein like structures will be provided with like reference designations.

It is to be appreciated that the present invention has application on many different types of tubing. The present invention, however, has particular application when used with tubing regularly found in the medical arts. Thus, the presently preferred embodiment described herein is one which is intended to be primarily used in connection with silicone rubber tubing commonly used in the medical arts.

Figure 1:
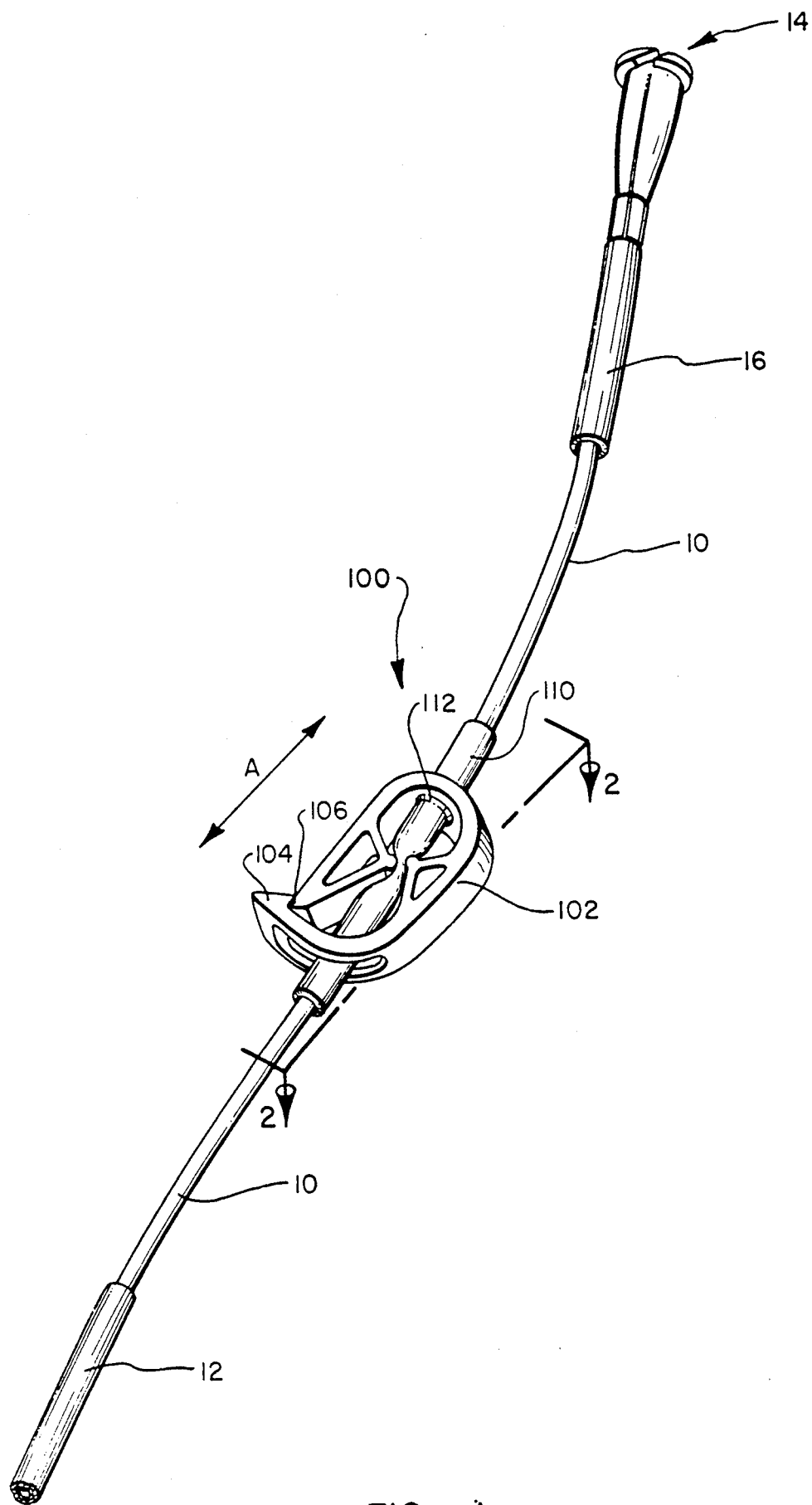
FIG. 1 is a perspective view of the presently preferred embodiment of the present invention fixed on a length of resilient tubing and occluding the same.

Referring first to FIG. 1, a length of tubing 10 with the presently preferred embodiment of the present invention attached thereto, generally designated 100, is illustrated in a perspective view. The length of tubing 10 is provided with a connector, generally designated at 14, at a first end. Connector 14 is of the type that is commonly used in the medical arts to join lengths of tubing to other medical devices and when the tubing is used as a portion of an indwelling catheter set.

Figure 2:
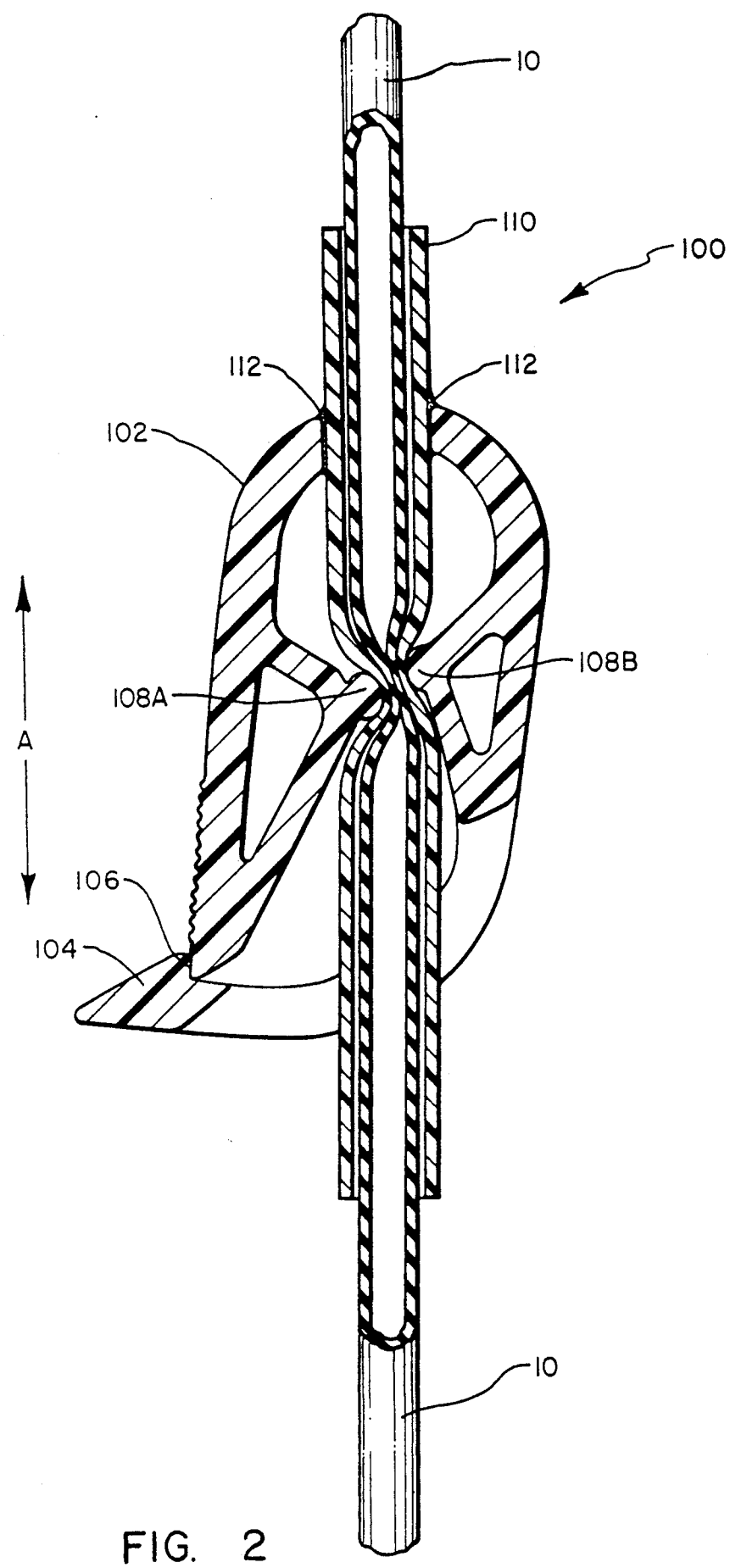
FIG. 2 is an elevated cross sectional view taken along line 2—2 in FIG. 1 of the presently preferred embodiment of the present invention.

Tubing 10 may have a single internal lumen (as represented in FIG. 2) or a plurality of internal lumens. Generally, as the number of internal lumens or channels increases, so does the tubing's susceptibility to clamping damage. Moreover, as the wall thickness of the tubing decreases, such as in small diameter and flexible thin wall catheters, the tubing's susceptibility to clamping damage increases.

While tubing 10 represented in FIG. 1 is cylindrical and described as silicone rubber medical tubing, tubing of different shapes, for example a substantially cylindrical shape such as an oval, or some noncircular shape, are well suited for use with the present invention. Also, tubing 10 of different materials have application with the present invention.

Also provided on tubing 10 is a semiflexible sleeve 16 which is generally included to reinforce and protect the tubing 10 where it attaches to connector 14. In general, tubing is particularly susceptible to breakage due to undue flexing where the tubing joins to connectors such as that represented at 14. In order to reduce failure at such points, structures such as semiflexible sleeve 16 are included but the tubing is still susceptible to breakage where the tubing exits the semiflexible sleeve. Another sleeve 12 is also provided on the tubing 10.

A compressive clamp body is also illustrated in FIG. 1 at 102. The clamp body may be patterned after any one of several tubing clamps known and readily available in the art and the illustrated structure is merely one example of the means for compressing the wall of the resilient tubing included in the present invention.

Any clamping structure which functions to occlude a length of tubing by compressing the wall of the tubing is intended to be equivalent to the pertinent structure illustrated in the drawings. For example, clamps incorporating pivoting structures as well as reciprocating structures may be used. Such clamps may utilize a flexible body as represented in the figures, a screw arrangement, or some other arrangement. The structure of compressive clamp body 102 is preferred because tubing 10 can be routed through apertures provided in clamp body 102.

Also represented in FIG. 1 is a protective sleeve 110. Protective sleeve 110 is the presently preferred example of the means for protectively covering of the present invention. Protective sleeve 110 is a cylindrical layer of a resilient material which encompasses a portion of tubing 10. It is, however, within the scope of the present invention to utilize configurations other than that represented in the figures including those which do not encompass or encircle the tubing but are merely interposed between the clamping structures and the tubing.

Depending upon the particular application the tubing is being put to, it may be preferred to fabricate the means for protectively covering from various resilient materials. For example, it may be preferred to utilize a material which is more or less hard, or more or less rigid, than the tubing to be protected.

Referring next to FIG. 2, the internal structure of the presently preferred embodiment of the invention 100 and tubing 10 can be seen in a cross sectional view. In FIG. 2, the inner diameter of protective sleeve 110 is represented to be slightly larger than the outer diameter of tubing 10. Importantly, in the illustrated embodiment, providing protective sleeve 10 with a slightly larger inner diameter than the outer diameter of tubing 10 allows protective sleeve 110 to slide along the length of tubing 10 in the directions of arrow A.

Providing protective sleeve 110 with the appropriate inner diameter allows protective sleeve 110 to be positioned at any one of a plurality of positions along the length of tubing 10. The structures which serve as protective sleeve 110, and its equivalent structures, may be of many different shapes. Such shapes may include those which are similar and those which are dissimilar to the shape of tubing 10.

Still referring to FIG. 2, compressive clamp body 102 is joined to protective sleeve 110 by an adhesive material represented at 112. The use of an adhesive material to join compressive clamp body 102 to protective sleeve 110 is preferred since the compressive clamp body and the protective sleeve are usually fabricated from dissimilar materials. It is, however, within the scope of the present invention to fabricate the compressive clamp body and the protective sleeve from appropriate similar materials and form the apparatus as a unitary structure with the joint between the clamping structures and the protective structures functioning as the means for connecting these structures. The adhesive joint represented at 112 is one example of a means for connecting the means for compressing to the means for protectively covering.

The means for connecting the compressive clamp to the protective sleeve functions to ensure that the means for protectively covering is interposed between tubing 10 and the pertinent structures of the clamp. By joining the compressive clamp to protective sleeve 110, tubing 10 will not be clamped without protective sleeve 110 being interposed between the tubing and the clamp. This provides a significant advance over the previously available devices intended to prevent clamping damage to tubing.

As previously mentioned, the portions of tubing which are immediately adjacent to connectors, joints, and other discontinuities in the tubing are generally more susceptible to breakage than other portions. In order to prevent clamping too close to connectors and other similar structures, such as those identified at 12 and 16 in FIG. 1, the length of protective sleeve 110 may be extended a predetermined distance beyond compressive clamp body 102.

By extending the length of protective sleeve 110 beyond the compressive clamp body a predetermined amount, clamp body 102 may be kept a desired distance away from connectors such as 14 shown in FIG. 1 or from other discontinuities present in the length of tubing. Generally, any increase in the diameter of the tubing will serve as a stop structure for the protective sleeve. Alternatively, a connector structure 14 or a sleeve 16 as shown in FIG. 1 can function as a stop structure.

It will be appreciated that structures other than the illustrated protective sleeve 110 may function to limit the proximity with which clamp body 102 may be applied to tubing 10 adjacent to connectors and the like. Also, the particular portion of tubing 10 to which the clamp may be applied can be suitably limited. Thus, if it is desired to keep clamp body 102 between two points on tubing 10, raised ridges or other similar functioning stop structures may be formed on the outer surface of tubing 10.

As can be seen best in FIG. 2, occlusion of tubing 10 is accomplished by placing lever end 106 under pawl 104 causing compressing structures 108A and 108B to squeeze the wall of protective sleeve 110 and tubing 10 thus occluding the tubing's internal channel. The clamp can be released from its closed configuration (as shown in the figures) to its open configuration by releasing lever end 106 from under pawl 104. It will be appreciated that the design of the compressing structures of the clamp will be one of the considerations to be recognized when choosing the material for protective sleeve 110 and its shape, thickness, resiliency, and other characteristics.

After consideration of the foregoing, it will be appreciated that the present invention provides a great advance over previously available devices. The embodiments of the present invention each include a protective structure, such as a protective sleeve, which is interposed between the resilient tubing and the clamp to protect the tubing from damage.

The protective and clamping structures included in the preferred embodiments are arranged such that they cannot be removed from the resilient tubing. Thus, the embodiments of the present invention cannot be inadvertently defeated by a user or misplaced. Furthermore, the embodiments of the present invention allow clamping to occur at any of a number of positions along the length of the tubing, thus preventing potential damage to the tubing from repeated clamping at any one position.

Still further, embodiments of the present invention may be adapted to restrict clamping within a predetermined distance of particular locations along the tubing which might be particularly susceptible to clamping damage. Overall, the present invention provides many advantages not heretofore known in the art.

The present invention may be embodied in other specific forms without departing from its spirit or essential characteristics. The described embodiment is to be considered in all respects only as illustrative and not restrictive. The scope of the invention is, therefore, indicated by the appended claims rather than by the foregoing description. All changes which come within the meaning and range of equivalency of the claims are to be embraced within their scope.

What is claimed and desired to be secured by United States Letters Patent is:

1. An apparatus for occluding resilient tubing to interrupt the flow of a fluid therethrough, the apparatus comprising:
   (a) means for compressing the resilient tubing by urging together opposing walls thereof, the means for compressing being capable of assuming an open and a closed configuration and having compressing structures adapted to produce mutually opposed forced for urging together opposing walls of the resilient tubing when the means for compressing is in the closed configuration;
   (b) means for protectively covering at least a portion of the circumference of the resilient tubing with a layer of resilient material, the means for protectively covering being positionable at any one of a plurality of positions along the length of the resilient tubing; and
   (c) means for permanently connecting the means for compressing to the means for protectively covering, such that the means for protectively covering is interposed between the resilient tubing and the compressing structure whenever the means for compressing is in its closed configuration in any of said plurality of positions along the length of the tubing, thereby minimizing damage to any particular position on the resilient tubing due to the repeated compressing of the resilient tubing by the means for compressing.

2. An apparatus for occluding resilient tubing to interrupt the flow of a fluid therethrough as defined in claim 1 wherein the means for protectively covering comprises a protective sleeve encircling the resilient tubing, the protective sleeve being compressible against.

3. An apparatus for occluding resilient tubing to interrupt the flow of a fluid therethrough as defined in claim 2 wherein the protective sleeve comprises a resilient material.

4. An apparatus for occluding resilient tubing to interrupt the flow of a fluid therethrough as defined in claim 3 wherein the resilient material has substantially the same characteristics as the material forming the resilient tubing.

5. An apparatus for occluding resilient tubing to interrupt the flow of a fluid therethrough as defined in claim 1 wherein the means for permanently connecting comprises an adhesive joint.

6. An apparatus for occluding resilient tubing to interrupt the flow of a fluid therethrough as defined in claim 1 wherein the resilient tubing comprises substantially cylindrical tubing, and wherein the means for protectively covering comprises a circumferentially continuous cylindrical protective sleeve encircling the outer circumference of the resilient tubing, the protective sleeve having an inner diameter greater than the diameter of the resilient tubing, such that the protective sleeve is slidable along the length of the tubing and the protective sleeve is compressible against the walls of the resilient tubing by the mutually opposed forces produced by said means for compression.

7. An apparatus for occluding resilient tubing to interrupt the flow of a fluid therethrough as defined in claim 6 wherein the means for compression is permanently connected to the protective sleeve such that the mutually opposed forces produced by the means for compressing are applied at a medial position on the length of the protective sleeve, thereby to preclude compression of the tubing any closer than a predetermined distance from a stop structure placed at a point along the tubing.

8. An apparatus for occluding resilient tubing to interrupt the flow of a fluid therethrough as defined in claim 1 wherein the means for compressing comprises a flexible clamp.

9. An apparatus for occluding resilient tubing to interrupt the flow of a fluid therethrough as defined in claim 1 wherein the resilient tubing comprises silicone rubber tubing having a diameter of less than one half inch.

10. An apparatus for occluding resilient tubing to interrupt the flow of a fluid therethrough as defined in claim 1 wherein the resilient tubing comprises tubing having a plurality of internal lumens.

11. An apparatus for occluding resilient tubing to interrupt the flow of a fluid therethrough as defined in claim 7 further comprising:
  (a) a first stop structure positioned at a first location along the resilient tubing, the first stop structure having a cross sectional dimension which is greater than the inner diameter of the protective sleeve; and
  (b) a second stop structure positioned at a second location along the resilient tubing, the second stop structure having a cross sectional dimension which is greater than the inner diameter of the protective sleeve;
  whereby the means for protectively covering is permanently positioned between the first and the second stop structures and is selectively positionable at any one of a plurality of positions along the length of the resilient tubing between the first and the second stop structures.

12. An apparatus for occluding resilient tubing to interrupt the flow of a fluid therethrough as defined in claim 11 wherein the first stop structure is a connector positioned at the end of the length of the resilient and flexible tubing.

13. An apparatus for occluding resilient tubing comprising:
  (a) a protective sleeve disposed opposing a portion of the wall of the resilient tubing, the protective sleeve being compressible against the wall of the resilient tubing to occlude the tubing and being slidable along the length of the tubing; and
  (b) a clamp having a compressive structure and being permanently attached to a medial position on the protective sleeve, said compressive structure of the clamp being adapted in a closed configuration thereof to selectively effect a compressible contact through the protective sleeve against the wall of the resilient tubing, the protective sleeve being always interposed between the compressive structure of the clamp and the resilient tubing within the sleeve, and the sleeve being movable along the length of the resilient tubing to allow the compressive contact of the clamp to be applied to a plurality of points along the length of resilient tubing, thereby to avoid damage at any particular position on the resilient tubing.

14. An apparatus for occluding resilient tubing as defined in claim 13 wherein the resilient tubing comprises a substantially cylindrical tubing and wherein the protective sleeve comprises a circumferentially continuous cylindrical protective sleeve encircling the circumference of the resilient tubing, the protective sleeve having an inner diameter greater than the diameter of the resilient tubing, such that the protective sleeve is slidable along the length of the tubing and such that the protective sleeve is compressible against upon the wall of the resilient tubing in the closed configuration of the clamp.

15. An apparatus for occluding resilient tubing as defined in claim 13 wherein the protective sleeve extends longitudinally in both directions of said compressive structure beyond the length of the clamp, the clamp thereby being precluded from assuming its closed configuration closer than a predetermined distance from any stop structure located along the length of the flexible tubing.

16. An apparatus for occluding resilient tubing as defined in claim 13 wherein the compressive clamp comprises a flexible clamp body and wherein the resilient tubing comprises silicone rubber tubing having a diameter of less than one half inch.

17. An apparatus for occluding resilient tubing as defined in claim 13 wherein the resilient tubing comprises tubing having a plurality of internal lumens.

18. An apparatus for occluding resilient tubing as defined in claim 15 further comprising:
  (a) a first stop structure positioned at a first location along the resilient tubing, the first stop structure having a cross sectional dimension which is greater than the inner diameter of the protective sleeve; and
  (b) a second stop structure positioned at a second location along the resilient tubing, the second stop structure having a cross sectional dimension which is greater than the inner diameter of the protective sleeve;
  whereby the protective sleeve is permanently positioned between the first and the second stop structures and is selectively positionable at any one of a plurality of positions along the length of the resilient tubing between the first and the second stop structures.

19. An apparatus for occluding resilient tubing as defined in claim 18 wherein the first stop structure is a connector positioned at the end of the length of the resilient tubing.

20. An apparatus for occluding resilient tubing as defined in claim 13 wherein the resilient tubing is a portion of a catheter set.

21. A device to stop the flow of a fluid through a length of resilient tubing comprising:
  (a) a clamp capable of selectively assuming an opened configuration and a closed configuration in which mutually opposed forces are imposed on the walls of the resilient tubing;
  (b) a sleeve adapted to slidably encircle the wall of the resilient tubing, the sleeve being compressible against the cross sectional dimension of the resilient tubing by said mutually opposed forces to occlude the passage of a fluid through the tubing;

(c) means for permanently attaching the clamp to the sleeve such that the occluding contact of the clamp is always imposed upon the sleeve; and (d) two stop structures each having a cross sectional dimension greater than the resilient tubing and the inner diameter of the protective sleeve, the stop structures being spaced apart from one another and adapted for restricting the removal the clamp from the portion of the length of tubing therebetween.

22. A device to stop the flow of a fluid through a length of resilient tubing as defined in claim 21 wherein the means for attaching the clamp to the sleeve comprises an adhesive joint between the clamp and the sleeve.

23. A device to stop the flow of a fluid through a length of resilient tubing as defined in claim 21 wherein the resilient tubing comprises a substantially cylindrical tubing and wherein the sleeve has an inner diameter that is greater than the outer diameter of the resilient tubing.

24. A device to stop the flow of a fluid through a length of resilient tubing as defined in claim 21 wherein the protective sleeve extends longitudinally along the flexible tubing in both directions beyond the length of the clamp, the clamp thereby being precluded from assuming its closed configuration closer than a predetermined distance from either of the stop structures.

25. A device to stop the flow of a fluid through a length of resilient tubing as defined in claim 21 wherein the clamp comprises a flexible clamp body and wherein the resilient tubing comprises silicone rubber tubing having a cross sectional dimension of less than one half inch.

26. A device to stop the flow of a fluid through a length of resilient tubing as defined in claim 21 wherein the resilient tubing comprises tubing having a plurality of internal lumens.

27. A device to stop the flow of a fluid through a length of resilient tubing as defined in claim 21 wherein one of the two stop structures is a connector positioned at the end of the length of resilient tubing.

28. A device to stop the flow of a fluid through a length of resilient tubing as defined in claim 21 wherein the resilient tubing is a portion of a catheter set.

* * * * *

UNITED STATES PATENT AND TRADEMARK OFFICE
CERTIFICATE OF CORRECTION

PATENT NO. : 5,035,399

DATED : July 30, 1991

INVENTOR(S) : ANN M. RANTANEN-LEE

It is certified that error appears in the above-identified patent and that said Letters Patent is hereby corrected as shown below:

```
Column 1, line 39, "at least" should be --at the least--
Column 2, line 40, delete "24"
Column 2, lines 40-47, "Included in the present . . . tubing."
should be a new paragraph
Column 6, line 20, "forced" should be --forces--
Column 6, line 45, after "against" insert --the resilient
tubing by the mutually opposed forces produced by said means
for compressing--
Column 7, lines 49-50, delete "and flexible"
Column 8, line 14, delete "upon"
```

Signed and Sealed this

Twenty-fifth Day of May, 1993

Attest:

MICHAEL K. KIRK

*Attesting Officer*         *Acting Commissioner of Patents and Trademarks*